United States Patent [19]

Bonk

[11] Patent Number: 5,677,463

[45] Date of Patent: Oct. 14, 1997

[54] PROCESS FOR THE PREPARATION OF 2-IMINO-5-PHENYL-4 OXAZOLIDINONE AND ITS INTERMEDIATES

[75] Inventor: Peter J. Bonk, Kenosha, Wis.

[73] Assignee: Abbott Laboratories, Abbott Park, Ill.

[21] Appl. No.: 754,772

[22] Filed: Nov. 20, 1996

[51] Int. Cl.$^6$ ..................... C07D 263/36
[52] U.S. Cl. ............................. 548/225
[58] Field of Search ........................ 548/225

[56] References Cited

U.S. PATENT DOCUMENTS

| | | | |
|---|---|---|---|
| 2,892,753 | 6/1959 | Schmidt et al. | 167/65 |
| 5,143,927 | 9/1992 | Boschelli et al. | 514/369 |
| 5,143,929 | 9/1992 | Belliotti et al. | 514/364 |
| 5,250,552 | 10/1993 | Boschelli et al. | 514/376 |

*Primary Examiner*—Joseph McKane
*Attorney, Agent, or Firm*—Michael J. Ward

[57] ABSTRACT

The present invention relates to the production of pemoline and its intermediates.

21 Claims, 1 Drawing Sheet

PROCESS FOR THE PREPARATION OF 2-IMINO-5-PHENYL-4 OXAZOLIDINONE AND ITS INTERMEDIATES

FIELD OF THE INVENTION

The present invention relates to a novel process for the production of pemoline and its intermediates.

BACKGROUND OF THE INVENTION

Stimulating amines derived from β-phenyl ethylamines and their derivatives are effective central nervous system stimulants. These compounds not only have central nervous stimulating effects, but also can produce an increase in arterial blood pressure as well as act as appetite depressants. However, they can be habit-forming with continual use. In addition, administration of these stimulants can raise tolerances whereby progressively increased dosages may be necessary to obtain the same effect.

Stimulating amines may be contraindicated in hypertonic and psychically unstable patients in whom habituation to such stimulating amines may occur.

A compound, 2-imino-5-phenyl-4-oxazolidinone, otherwise known as pemoline, has a central nervous stimulating effect while being substantially free of objectionable side effects which the stimulating amines typically cause. Pemoline, for instance, does not produce euphoristic effects.

The pemoline compound is prepared, as described in U.S. Pat. No. 2,892,753 to Schmidt, et al., by reacting mandelic acid ethyl ester with guanidine in a boiling alcoholic solution which produces a pemoline precipitate. However, the use of guanidine in the reaction has its disadvantages including impurities in the final product.

There continues to be a need for more efficient routes of synthesis producing high, pure yields of pemoline.

SUMMARY OF THE INVENTION

The present invention provides a novel process for the preparation of pemoline and its salts, as well as intermediates used in the preparation of pemoline. An alkyl mandelate and a cyanamide-containing compound are dissolved in a solvent to form a reaction mixture. A sodium alkoxide solution is added to the reaction mixture, followed by acidification of the reaction mixture.

DETAILED DESCRIPTION OF THE FIGURES

Figure 1:
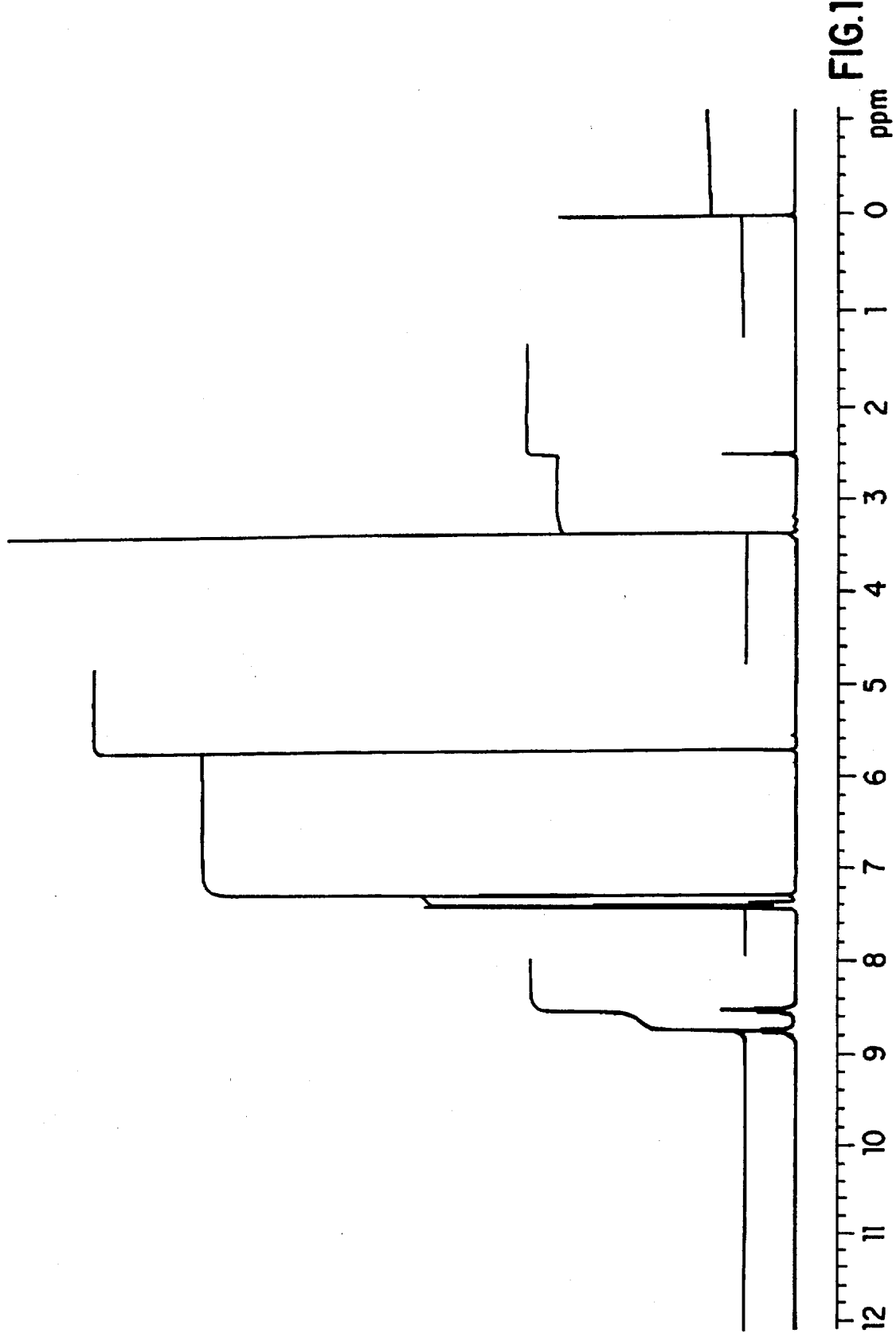

FIG. 1 is the $^1$H NMR spectrum of 2-imino-5-phenyl-4-oxazolidinone prepared by the process of the present invention.

DETAILED DESCRIPTION OF THE INVENTION

The present invention provides a process for the preparation of 2-imino-5-phenyl-4-oxazolidinone (Pemoline) as well as the preparation of intermediates of pemoline.

One embodiment of the present invention involves reacting a cyanamide-containing compound in a sodium alkoxide solution to form a reaction mixture. The reaction mixture is then added to an alkyl mandelate/solvent solution. The resultant reaction mixture is then acidified to a pH of 6.0 or less to precipitate a pemoline product.

In another embodiment of the present invention, a solvent is added to a reaction flask that contains cyanamide. An alkyl mandelate is then added to the reaction flask. A sodium alkoxide solution is then added to the reaction flask to form a reaction mixture. The reaction mixture is cooled and acidification of the reaction mixture is done slowly. The reaction mixture is acidified to a pH of about 6.0 or less. Acidification of the reaction mixture precipitates out a pemoline/salt mixture. The precipitate may optionally be rinsed with distilled water to removes any salt.

In yet another embodiment of the present invention, a cyanamide-containing compound is added to a sodium alkoxide solution. An alkyl mandelate is added to the mixture and the mixture is heated at reflux, cooled, and acidified slowly to a pH of about 6.0 or less. More preferably, the mixture is acidified to a pH of 4.0 or less.

Alkyl mandelate compounds suitable for use with the process of the present invention include, but are not intended to be limited to, methyl mandelate and ethyl mandelate. A preferred alkyl mandelate is methyl mandelate.

Cyanamide containing compounds suitable for use with the process of the present invention include, but are not intended to be limited to, cyanamide and dicyanamide.

Solvents suitable for dissolving the alkyl mandelate and cyanamide-containing compound include, but are not intended to be limited to, alkanols including methanol, ethanol, propanol, iso-propanol, and hexanol. Preferred alkanol solvents are methanol, ethanol and iso-propanol.

Sodium alkoxide solutions suitable for the present invention include, but are not intended to be limited to, sodium methoxide and sodium ethoxide. A preferred sodium alkoxide is sodium methoxide. The alkoxide solutions and powders may be obtained commercially. Alternatively, sodium metal may be added to a solvent, such as methanol, and heated at reflux temperature.

EXAMPLE 1

Sodium methoxide was prepared by adding methanol (200 milliliters (mL)) to a reaction flask. The reaction flask was equipped with a magnetic stirrer, a thermocouple which was connected to a controller, and an $N_2$ inlet atop a reflux condenser. Sodium metal (15.1 grams, 0.6 moles) (Aldrich Chemical Co., Inc., Milwaukee, Wis.) was added to the methanol and the exothermic reaction quickly heated itself to reflux (67° C.). The reaction mixture was heated at reflux for 20 minutes and approximately 75 mL of methanol was distilled.

The reaction mixture was cooled to <10° C. in an ice bath. Cyanamide (25.4 grams, 0.6 mole) (SKW Chemicals, Inc., Marietta, Ga.) was added to the reaction mixture and then 18 mL of methanol were added. The reaction mixture was stirred at <10° C. for 120 minutes.

A methyl mandelate solution was prepared by dissolving methyl mandelate (99.7 grams, 0.6 mole) (Aldrich Chemical Co., Inc., Milwaukee, Wis.) in 100 mL of methanol in a 1000 mL three neck round bottom flask equipped with an overhead mechanical stirrer and $N_2$ inlet atop a reflux condenser.

The cyanamide/sodium methoxide reaction mixture was added to the solution of methyl mandelate over a period of one minute. Any residual cyanamide/sodium methoxide reaction mixture left in the original reaction flask was rinsed with 47 mL of methanol and added to the combined cyanamide/sodium methoxide/methyl mandelate mixture. The combined cyanamide/sodium methoxide/methyl mandelate mixture was heated to a reflux temperature of 66° C. for 2 hours, and then allowed to stir at room temperature overnight.

The reaction mixture was cooled in an ice bath to <10° C. Approximately 60 grams of concentrated hydrochloric acid (HCl) (0.6 mole) was added over 2 hours to adjust the pH to about 6.0 and precipitate a pemoline/chloride salt slurry. During acid addition, the temperature of the reaction mixture was kept at less than 12° C. due to the exothermic nature of the reaction. The reaction mixture was allowed to stir at <12° C. for an additional 2 hours. The pemoline/chloride salt slurry was collected and additional methanol was added as needed to remove any pemoline/chloride salt slurry from the flask. The pemoline/chloride salt slurry was air dried for 30 minutes and then the wet cake was weighed (240 grams). The wet cake was added to a flask with 300 mL water, stirred for 30 minutes, and then collected in a Buchner funnel. The wet cake was washed with 150 mL of water and allowed to dry on the filter overnight.

The wet cake was washed with methanol and allowed to dry on the filter paper for 2 hours. The wet cake (149 grams) was collected and dried in a vacuum oven at 75°–80° C. overnight.

After drying in the vacuum oven, the dried cake weighed 90.3 grams. HPLC analysis of the dried cake indicated that it was 99.87% pure with 0.13 area percent of mandelic acid.

EXAMPLE 2

In a 2 liter, three neck jacketed round bottom reaction flask equipped with an overhead mechanical stirrer, an $N_2$ inlet atop a reflux condenser, an addition funnel, and a thermocouple, 41 grams of cyanamide (0.975 mole) was added. Methanol (200 mL) was added to the reaction flask. To this reaction mixture was added 162 grams of racemic methyl mandelate (0.975 mole) followed by a 10 mL rinse of methanol. The reaction mixture was allowed to stir at 0° C. to 5° C. until all the solids had dissolved. To the reaction mixture was added 216 grams of a 25% methanolic sodium methoxide (54 grams, 1.0 mole of contained sodium methoxide) solution via the addition funnel, keeping the reaction temperature at <6° C. Addition of the 25% methanolic sodium methoxide solution took 25 minutes. The reaction mix was stirred at 0° C.±5° C. overnight while maintaining a nitrogen purge.

Concentrated hydrochloric acid (82 mL) was added to the reaction mixture to achieve a pH of approximately 3.0. The reaction mixture was stirred for one hour and kept at a temperature of 0° to 5° C. distilled water (240 mL) was added and the reaction mixture was stirred for an additional 90 minutes at a temperature of approximately 0° C.

The reaction mixture solids were collected by vacuum filtration and washed with water (about 5.5 liters) to remove salt. The solids were rinsed with 200 mL of methanol and allowed to air dry overnight. The solids were then dried in a vacuum oven at 105° C. for 4 hours to give 146.2 grams of pemoline which amounted to a 85% yield.

EXAMPLE 3

Methanol (195 mL) was added to a 1 liter, four neck jacketed round bottom reaction flask equipped with an overhead mechanical stirrer, an $N_2$ inlet atop a reflux condenser, an addition funnel, and a thermocouple. Sodium metal (12.2 grams) was slowly added to form a sodium methoxide solution and the solution was cooled to approximately 14° C. Cyanamide (21.05 grams, 0.501 moles) was added to the sodium methoxide solution and the reaction mixture was stirred for 30 minutes.

Racemic methyl mandelate (83.1 grams, 0.500 moles) was added to the reaction mixture while stirring. The reaction mixture was heated to reflux temperature for 60 minutes. The reaction mixture was cooled to approximately 14° C. and then 150 mL of distilled water was added. The reaction mixture was cooled to approximately 8° C. and then concentrated hydrochloric acid (49 mL) was added to achieve a pH of 2.0. The concentrated hydrochloric acid was added over a period of 30 minutes. The reaction mixture was stirred for 60 minutes at a temperature of approximately 10° C. The solids formed were collected by vacuum filtration and were washed with approximately 4 liters of chilled distilled water. The solids were rinsed with 150 mL of chilled methanol and allowed to air dry overnight. The solids were oven dried for 4 hours at a temperature of 105° C. The net weight of the dried pemoline solids was 75.17 grams (85% yield).

What is claimed:

1. A process for the preparation of an intermediate of 2-imino-5-phenyl-4-oxazolidinone comprising the steps of:

(a) adding a cyanamide-containing compound to an sodium alkoxide solution to form a reaction mixture; and (b) adding said reaction mixture to an alkyl mandelate solution.

2. A process according to claim 1 wherein said alkyl mandelate is selected from methyl mandelate and ethyl mandelate.

3. A process according to claim 1 wherein said alkyl mandelate is methyl mandelate.

4. A process according to claim 1 wherein said solvent is selected from methanol, ethanol, propanol, iso-propanol, and hexanol.

5. A process according to claim 1 wherein said solvent is selected from methanol, ethanol, and iso-propanol.

6. A process according to claim 1 wherein said sodium alkoxide solution is selected from sodium methoxide and sodium ethoxide.

7. A process according to claim 1 wherein said alkyl mandelate solution is added to said reaction mixture.

8. A process for the preparation of an intermediate of 2-imino-5-phenyl-4-oxazolidinone comprising the steps of:

(a) dissolving an alkyl mandelate and a cyanamide-containing compound in a solvent to form a reaction mixture; and (b) adding a sodium alkoxide solution.

9. A process according to claim 8 wherein said alkyl mandelate is selected from methyl mandelate and ethyl mandelate.

10. A process according to claim 8 wherein said alkyl mandelate is methyl mandelate.

11. A process according to claim 8 wherein said solvent is selected from methanol, ethanol, propanol, iso-propanol, and hexanol.

12. A process according to claim 8 wherein said solvent is selected from methanol, ethanol, and iso-propanol.

13. A process according to claim 8 wherein said sodium alkoxide solution is selected from sodium methoxide and sodium ethoxide.

14. A process for preparation of 2-imino-5-phenyl-4-oxazolidinone comprising the steps of;

(a) dissolving an alkyl mandelate and a cyanamide-containing compound in a solvent to form a reaction mixture;

(b) adding a sodium alkoxide solution; and (c) acidifying the reaction mixture.

15. A process according to claim 14 wherein said alkyl mandelate is selected from methyl mandelate and ethyl mandelate.

16. A process according to claim 14 wherein said alkyl mandelate is methyl mandelate.

17. A process according to claim 14 wherein said solvent is selected from methanol, ethanol, propanol, iso-propanol, and hexanol.

18. A process according to claim 14 wherein said solvent is selected from methanol, ethanol, and iso-propanol.

19. A process according to claim 14 wherein said acidification of said reaction mixture results in a pH of about 6.0 or less.

20. A process according to claim 14 wherein said acidification of said reaction mixture results in a pH of about 4.0 or less.

21. A process according to claim 14 wherein said sodium alkoxide solution is selected from sodium methoxide and sodium ethoxide.

* * * * *